United States Patent [19]

Laurent

[11] Patent Number: 5,719,168
[45] Date of Patent: Feb. 17, 1998

[54] ACETAMIDE DERIVATIVES AND THEIR USE AS FEEDING BEHAVIOUR MODIFIERS

[75] Inventor: Philippe Laurent, Oullins, France

[73] Assignee: Laboratoire L. Lafon, Maisons Alfort, France

[21] Appl. No.: 564,284

[22] PCT Filed: Jun. 30, 1994

[86] PCT No.: PCT/FR94/00803

§ 371 Date: Apr. 22, 1996

§ 102(e) Date: Apr. 22, 1996

[87] PCT Pub. No.: WO95/01333

PCT Pub. Date: Jan. 12, 1995

[30] Foreign Application Priority Data

Jun. 30, 1993 [FR] France ................ 93 08008

[51] Int. Cl.$^6$ .............. C07D 213/56; C07C 317/44; A61K 31/16; A61K 31/44
[52] U.S. Cl. ............ 514/357; 514/352; 514/618; 546/309; 546/333; 564/162
[58] Field of Search ............ 546/309, 333; 564/162; 514/352, 357, 618

[56] References Cited

FOREIGN PATENT DOCUMENTS

| | | |
|---|---|---|
| 2385693 | 10/1978 | France . |
| 2528038 | 12/1983 | France . |
| 2602768 | 2/1988 | France . |

OTHER PUBLICATIONS

Copy of PCT International Search Report, 1994.

*Primary Examiner*—Zinna Northington Davis
*Attorney, Agent, or Firm*—Jacobson, Price, Holman & Stern, PLLC

[57] ABSTRACT

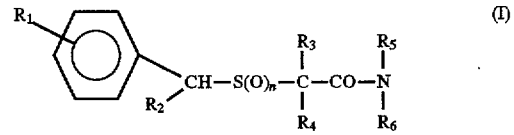

The present invention relates to compounds of formula (I) wherein $R_1$ is selected from H and 3-chloro; $R_2$ is selected from a phenyl group and a pyridyl group; $R_3$ and $R_4$ are selected independently of each other from H and methyl; $R_5$ and $R_6$ are selected independently of each other from H and a pyridyl-methyl group or both represent an ethyl group; $n=0$ or 1; $R_1$, $R_3$, $R_4$, $R_5$ and $R_6$ are not simultaneously H when $R_2$ is phenyl. The salts of the compounds have a pyridyl group with pharmaceutical acceptable acids are also disclosed.

9 Claims, No Drawings

ACETAMIDE DERIVATIVES AND THEIR USE AS FEEDING BEHAVIOUR MODIFIERS

This application is a 371 of PCT/FR94/0083 filed Jun. 30, 1994.

The present invention relates to acetamide derivatives which may be used therapeutically as feeding behaviour modifiers.

Various acetamide derivatives which may be used therapeutically are already known for their stimulatory effect on the central nervous system. Mention may be made in particular of adrafinil or benzhydrylsulphinyl acetohydroxamic acid (described in FR-A-2,326,181) and modafinil (described in FR-A-2,385,693) and other compounds described in FR-A-2,528,038, FR-A-2,601,673, FR-A-2,602,768 and FR-A-2,606,815.

The present invention aims to provide novel acetamide derivatives which are characterized by a modificatory or regulatory effect on feeding behaviour in man and animals.

The subject of the present invention is thus compounds of formula:

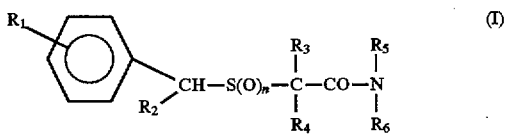

in which:

$R_1$ is chosen from H and 3-chloro, $R_2$ is chosen from a phenyl group and a pyridyl group, $R_3$ and $R_4$ are chosen, independently of each other, from H and methyl, $R_5$ and $R_6$ are chosen, independently of each other, from H and a pyridylmethyl group or both represent an ethyl group, n=0 or 1, $R_1$, $R_3$, $R_4$, $R_5$ and $R_6$ not simultaneously being H when $R_2$=phenyl, and the salts of the pyridyl-group-containing compounds with pharmaceutically acceptable acids.

The compounds of formula I may generally be obtained according to known methods. Thus, the compounds of formula I in which n=1 may be obtained by oxidation, in particular by $H_2O_2$, of a compound of formula I in which n=0, that is to say a thioacetamide of formula:

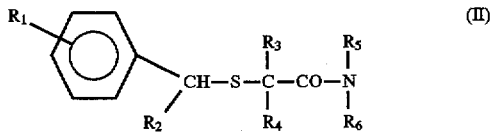

The thioacetamides of formula II may be obtained in particular by reaction of a reactive derivative of an acid of formula:

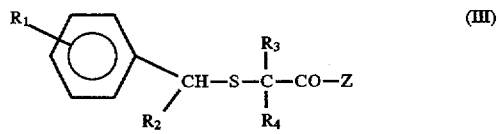

in which Z is a reactive group, in particular Cl or $OCH_3$, with an amine of formula:

$HNR_5R_6$ 

As a variant, certain compounds may be obtained by reaction of an acid of formula:

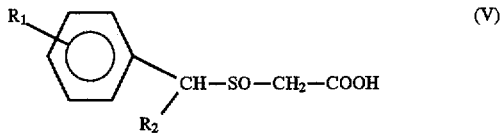

or one of the reactive derivatives thereof, with an amine of formula III.

The compounds according to the invention may be used therapeutically as feeding behaviour modifiers or regulators in man and animals.

Another subject of the present invention is thus therapeutic compositions comprising an effective amount of a compound of formula I or salts of compounds of formula I containing a pyridine group with pharmaceutically acceptable acids.

The therapeutic compositions according to the invention may be administered in particular via the oral route.

They may be in the form of solid or semi-solid preparations. Tablets, gelatin capsules and delayed-action forms may be mentioned as examples.

In these compositions, the active principal is generally mixed with one or more usual pharmaceutically acceptable excipients well known to those skilled in the art.

These compositions make it possible in particular to delay feeding and may thus constitute a valuable aid to weight control, in particular for individuals who are on a diet.

The effects on feeding behaviour have been demonstrated using a test in mice, according to a method described by Ladurelle et al. (Fundam. Clin. Pharmacol., 5, 481).

The examples which follow illustrate the preparation of the compounds of formula I.

EXAMPLE 1

Preparation of m-chlorobenzhydrylsulphinylacetamide (CRL 41096).

a) Preparation of m-chlorobenzhydrol

The following are placed in a three-necked flask: 4.86 g (0.2 g.at.) of magnesium covered with a small amount of anhydrous ether, a crystal of iodine and a few drops of bromobenzene are added in order to initiate the reaction; a solution of 32 g (0.204 mol) of bromobenzene in 200 ml of ether is then added dropwise. The mixture is then maintained at reflux on a water bath for about 1 hour, followed by cooling and dropwise addition, when cold, of a solution of 28.1 g (0.2 mol) of m-chlorobenzaldehyde in a small amount of ether. The complex thus obtained is filtered and then taken up in ether and hydrolysed with a water+HCl solution. The ether phase is then washed with water, dried over $Na_2SO_4$ and evaporated.

28.14 g of a yellow oil are collected: m-chlorobenzhydrol (yield=65%).

b) Preparation of m-chlorobenzhydrylthioacetic acid

The following are placed in a three-necked flask: 12.86 g (0.156 mol) of thiourea in 65 ml of 48% HBr and 13 ml of water; the mixture is brought to 60° C. and 28.4 g (0.13 mol) of m-chlorobenzhydrol are added in a single portion. The temperature is raised to 95° C. and the mixture is then left to cool: thiouronium hydrobromide precipitates out; this is drained and washed with water.

The salt thus obtained is taken up in 39 ml of 10N caustic soda (0.39 mol), the mixture is brought to 70° C. and a solution of 13.51 g (0.143 mol) of chloroacetic acid in a small amount of water is added dropwise.

The mixture is then brought to reflux, kept at reflux for ½ hour and then cooled: the sodium salt of the acid precipitates out.

The mixture is acidified directly with concentrated HCl, the oil thus obtained is extracted with ether, washed with dilute sodium hydroxide solution, filtered over charcoal and acidified again with concentrated HCl, and the precipitate thus obtained is drained and washed with water. After recrystallization from cyclohexane, this gives 29.29 g of m-chlorobenzhydrylthioacetic acid (m.p.$_{inst}$=97° C.; yield=77%).

c) Preparation of m-chlorobenzhydrylthioacetyl chloride 29.25 g (0.1 mol) of the acid obtained in b) are dissolved in 150 ml of thionyl chloride. The mixture is maintained at reflux for 1 hour then cooled and the benzene and excess thionyl chloride are evaporated off.

A yellow oil is collected (yield=100%).

d) Preparation of m-chlorobenzhydrylthioacetamide 50 ml of $NH_3$ dissolved in 60 ml of water are placed in a three-necked flask, the solution is cooled and the acid chloride obtained above (=0.1 mol) dissolved in about 125 ml of methylene chloride is added dropwise. The mixture is left to stand overnight at room temperature, then washed with dilute sodium hydroxide solution and then with water, dried over $Na_2SO_4$ and evaporated. An orange-yellow oil which crystallizes in water is collected.

27.5 g of m-chlorobenzhydrylthioacetamide are obtained (m.p.$_{inst}$=56° C.; yield=94%).

e) Preparation of m-chlorobenzhydrylsulphinylacetamide 26.23 g (0.09 mol) of the product obtained in d) are dissolved in 90 ml of acetic acid in a round-bottomed flask, and 9.5 ml of $H_2O_2$ (≈110 vol.) are added. The temperature rises to 45° C. and then falls again. The disappearance of the sulphide is monitored by chromatography, then $H_2O$ is added and the acetic acid is neutralized by addition of sodium bicarbonate, and the precipitate thus obtained is drained and washed with water. After recrystallization from ethanol, 14 g of m-chlorobenzhydrylsulphinylacetamide are collected (m.p.$_{inst}$=170° C.; yield=50%).

The product is a white powder which is insoluble in ether and ethyl acetate and slightly soluble in alcohols. Its solubility in water is less than 0.1%.

EXAMPLE 2

Preparation of N-diethylbenzhydrylsulphinylacetamide (CRL 40488)

a) Preparation of N-diethylbenzhydrylthioacetamide 50 ml (0.5 mol) of diethylamine in about 50 ml of ether are placed in a three-necked flask fitted with a condenser and a dropping funnel, and 27.2 g (0.998 mol) of benzhydrylthioacetyl chloride dissolved in about 100 ml of benzene are added dropwise. Once the addition is complete, water is added to the reaction mixture. The organic phase is washed with dilute sodium hydroxide solution, dilute hydrochloric acid and then water, dried over $Na_2SO_4$ and the solvent is evaporated off.

b) Preparation of N-diethylbenzhydrylsulphinylacetamide 24.42 g (0.078 mol) of the crude acetamide obtained above are placed in a round-bottomed flask, and 80 ml of acetic acid and 8 ml of $H_2O_2$ (about 100 vol.) are added. The mixture is left to stand overnight at room temperature. The acetic acid is evaporated off, the oil obtained is taken up in methylene chloride, washed with dilute sodium hydroxide solution, with dilute hydrochloric acid and then with water and dried over $Na_2SO_4$, the solvent is evaporated off, the residue is taken up in isopropyl ether and the product is thus crystallized. It is recrystallized from benzene and isopropyl ether and 16.6 g of N-diethylbenzhydrylsulphinylacetamide are collected (yield=65%; m.p.$_{inst}$=100°–101° C.).

The product is a white powder which is slightly soluble in ether and isopropyl ether, and soluble in alcohols and methylene chloride. Its solubility in water is less than 0.1%.

EXAMPLE 3

Preparation of α-(4-pyridyl)benzenesulphinylacetamide hydrochloride (CRL 41890)

a) Preparation of α-(4-pyridyl)benzyl chloride hydrochloride

To a solution of 27.75 g (0.15 mol) of (4-pyridyl)benzyl alcohol and 200 ml of chloroform is run in dropwise, at room temperature, a solution of 15.25 ml (0.2 mol) of $SOCl_2$ and 50 ml of $CH_2Cl_2$.

After three hours at reflux, the mixture is evaporated to dryness under vacuum, the residue is taken up in ethyl acetate, drained and dried, and the desired hydrochloride is obtained (m.p.=152°–154° C.) in a yield of 96%.

b) Preparation of α-(4-pyridyl)benzylthioacetic acid

A solution of 10.2 g (0.13 mol) of thiourea in 100 ml of water is heated to 40° C., 28.8 g (0.12 mol) of the hydrochloride obtained in a) are added and the mixture is heated at reflux for 10 minutes. A solution of 24 g (0.6 mol) of sodium hydroxide in 150 ml of water is added at 50° C. and the mixture is heated at reflux for 10 minutes.

The mixture is cooled to 50° C. and a solution of 12.6 g (0.132 mol) of chloroacetic acid, 10 g of $Na_2CO_3$ and 100 ml of water is run in dropwise. The mixture is then heated at reflux for i hour, cooled, extracted twice with 100 ml of ether, filtered over charcoal, precipitated with concentrated HCl, drained and dried.

The acid (m.p.=142° C.) is thus obtained in a yield of 56%.

c) Preparation of α-(4-pyridyl)benzylthioacetamide

A solution of 19.2 g (0.075 mol) of the acid obtained in b) in 300 ml of methanol and 10 ml of concentrated $H_2SO_4$ is heated at reflux for 8 hours, the methanol is evaporated off under vacuum and the residue is taken up in 500 ml of cold water, precipitated with $Na_2CO_3$, extracted with ether, washed with water, dried and evaporated under vacuum.

The methyl ester is dissolved in 100 ml of methanol and 50 ml of 28% aqueous ammonia solution are added; after leaving to stand for 48 hours, the mixture is evaporated to dryness under vacuum, taken up in 100 ml of water, drained and dried.

The amide (m.p.=126° C.) is obtained in a yield of 84%.

The base dissolved in methanol is quantitatively converted into the hydrochloride (m.p.=192°–194° C.) by addition of hydrochloric isopropanol.

d) Preparation of α-(4-pyridyl)benzylsulphinylacetamide 4-hydrochloride 9.3 g (0.03 mol) of the sulphide obtained in c) dissolved in 30 ml of acetic acid are oxidized by addition of 3 ml of 110-volume aqueous hydrogen peroxide solution. The mixture is stirred for 1 hour at about 45° C. and for 2 hours at 25° C., evaporated to dryness under vacuum, taken up in ethanol, drained and recrystallized from methanol.

The product is obtained in a yield of 76%.

It is in the form of white crystals.

It is soluble in water and methanol, and insoluble in ethanol, ether, acetone, etc.

It melts with decomposition at 182°–183° C.

EXAMPLE 4

Preparation of 2-(benzhydrylsulphinyl)propionamide (CRL 41163)

a) Preparation of 2-(benzhydrylthio)propionic acid 7.6 g (0.1 mol) of thiourea in 50 ml of water are placed in a three-necked flask and 18 ml (0.1 mol) of chlorodiphenylmethane are added in a single portion at 50°–60° C. The mixture is then heated to reflux and kept boiling for ¼ hour. The solution becomes clear. The mixture is then cooled, followed, at about 60° C., by dropwise addition of a solution of 16 g (0.4 mol) of sodium hydroxide in 25 ml of water. The mixture is then brought to reflux and kept at reflux for ½ h–¾ h, cooled and, at about 65°–70° C., a solution of about 0.14 mol of potassium 2-bromopropionate (obtained by neutralizing 21.5 g (i.e. 13 ml) of α-bromopropionic acid with 14.2 g of potassium bicarbonate) is added.

The mixture is then maintained at reflux for ½ hour and then cooled, acidified directly in the reaction medium with concentrated HCl, and the precipitate thus obtained is drained and washed with water.

The acid is purified by redissolving it while cold in dilute sodium hydroxide solution, the insoluble material is extracted with methylene chloride and the alkaline phase is filtered over charcoal and then acidified. The acid thus obtained is drained and washed with water.

20 g of 2-(benzhydrylthio)propionic acid are obtained. (m.p.$_{inst}$=148° C.; yield=75%).

b) Preparation of 2-(benzhydrylthio)propionyl chloride 19.04 g (0.07 mol) of the acid obtained in a) in 120 ml of benzene are placed in a three-necked flask, the mixture is brought to reflux (solution) and 18 ml of thionyl chloride are added dropwise. When the addition is complete, the reflux is maintained for one hour then the mixture is cooled and the benzene and excess thionyl chloride are evaporated off. A clear orange-coloured oil is collected (yield=100%).

c) Preparation of 2-(benzhydrylthio)propionamide 35 ml of aqueous ammonia solution are dissolved in 40 ml of water, the solution is cooled and the acid chloride obtained above (0.07 mol) dissolved in a small amount of methylene chloride is added dropwise. The mixture is left to stand overnight and the organic phase is then separated out after settling of the phases, [lacuna] with dilute sodium hydroxide solution so as to remove the traces of acid, washed with water to neutral pH, dried over $Na_2SO_4$ and evaporated, and the precipitate thus obtained is taken up in petroleum ether.

After recrystallization from ethanol, 12.82 g of 2-(benzylthio)propionamide are obtained. (m.p.$_{inst}$=110° C.; yield=68%).

d) Preparation of 2-(benzhydrylsulphinyl)propionamide 13.55 g (0.05 mol) of 2-(benzhydrylthio)propionamide are placed in a round-bottomed flask and 50 ml of acetic acid and 6.5 ml of $H_2O_2$ (≈110 v) are added. The temperature rises to 40° C. then falls again; when all of the sulphide has disappeared, the acetic acid is evaporated off, the residue is taken up in water and sodium bicarbonate and the precipitate thus obtained is drained and washed with water.

After crystallization from ethyl acetate, 8 g of 2-(benzhydrylsulphinyl)propionamide are collected. (m.p.$_{inst}$=141° C.; yield=60%).

The product is a white powder which is insoluble in ether and sparingly soluble in ethyl acetate, acetone and alcohols. Its solubility in water is less than 0.1%.

EXAMPLE 5

Preparation of 2-(benzhydrylsulphinyl)-2-isobutyramide (CRL 41412)

a) Preparation of 2-(benzhydrylthio)isobutyric acid

To a solution of 6 g (0.26 g.at.) of sodium in 500 ml of ethanol are added 40 g (0.2 mol) of diphenylmethanethiol followed by dropwise addition, over 1 hour, of 48.75 g (0.25 mol) of ethyl 2-bromoisobutyrate. The mixture is maintained at reflux for about 2 hours then the ethanol is evaporated off and the residue is taken up in ether, washed three times with water, dried and evaporated.

59.6 g of ethyl 2-(benzhydrylthio)isobutyrate are collected. The ester obtained above is then dissolved in 100 ml of ethanol, followed by dropwise addition, while cold, of 33.6 g (0.6 mol) of KOH in alcohol. The ethanol is then evaporated off and the residue is taken up in water (solution), filtered over C and acidified with concentrated HCl.

The acid is purified by redissolving it in dilute sodium hydroxide solution, and is again acidified.

After recrystallization from cyclohexane, 28 g of 2-(benzhydrylthio)isobutyric acid are obtained. (m.p.$_{inst}$=119° C.; yield=50%).

b) Preparation of 2-(benzhydrylthio)isobutyramide 25.74 g (0.09 mol) of the product obtained above are dissolved in 180 ml of benzene and, at reflux, 22.5 ml of thionyl chloride are added dropwise. The reflux is maintained for i hour then the mixture is cooled, the benzene is evaporated off, the acid chloride thus obtained is taken up in 100 ml of methylene chloride and a solution of 200 g of ice and 100 ml of aqueous ammonia solution are added dropwise thereto.

After leaving to stand overnight, the organic phase is washed with water, dried and evaporated; the precipitate thus obtained is washed with isopropyl ether and then drained.

15.1 g of 2-(benzhydrylthio) isobutyramide are collected. (m.p.$_{inst}$=140° C.; yield=59%).

c) Preparation of 2-(benzhydrylsulphinyl)isobutyramide 14.25 g (0.05 mol) of the amide obtained in b) are placed in a round-bottomed flask and 50 ml of acetic acid and 6 ml of $H_2O_2$(≈110 vol.) are added.

The temperature rises to 40° C. then falls again. The acetic acid is then evaporated off, the residue is taken up in isopropyl ether and the 2-(benzhydrylsulphinyl) isobutyramide is thus precipitated and drained.

After recrystallization from isopropyl alcohol, 9 g of 2-(benzhydrylsulphinyl)isobutyramide are obtained. (m.p.$_{dec}$=117° C.; yield=60%).

The product is a white powder which is insoluble in ether, slightly soluble in ethyl acetate and soluble in alcohols. Its solubility in water is about 0.1%.

EXAMPLE 6

Preparation of N-(2-pyridylmethyl) benzhydrylsulphinylacetamide (CRL 41936)

a) Preparation of N-(2-pyridylmethyl) benzhydrylsulphinylacetamide

To a suspension of 15.44 g (0.06 mol) of benzhydrylsulphinylacetic acid in 90 ml of methylene chloride are added 6.48 g (0.06 mol, i.e. 6.17 ml) of 2-aminomethylpyridine and 12.36 g (0.06 mol) of dicyclohexylcarbodiimide are added to the solution thus obtained. The mixture is heated at reflux for about 3 to 4 hours, then left to cool.

The following day, the precipitate obtained is filtered off, the methylene chloride is evaporated off, the residue is taken up in ether, washed with water and extracted with dilute HCl solution, the insoluble material is filtered off and the product is precipitated with concentrated NaOH solution and drained.

5 g of N-(2-pyridylmethyl)benzhydrylsulphinylacetamide are collected.

m.p.$_{not\ sharp}$=76° C.; yield=24%.

b) Preparation of N-(2-pyridylmethyl) benzhydrylsulphinylacetamide hydrochloride The salt is prepared in acetone by addition of hydrochloric isopropanol to a solution of the base obtained above. 4.2 g of N-(2-pyridylmethyl)benzhydrylsulphinylacetamide hydrochloride are collected.

m.p.$_{pasty}$=108° C.; yield=76%.

This is a beige-coloured powder which is insoluble in ether and ethyl acetate and soluble in water.

We claim:

1. A compound of the formula:

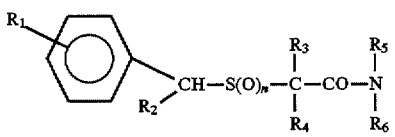

(I)

in which:

$R_1$ is selected from H and 3-chloro, $R_2$ is selected from phenyl and pyridyl, $R_3$ and $R_4$ are selected, independently of each other, from H and methyl, $R_5$ and $R_6$ are selected, independently of each other, from H or pyridylmethyl or both represent ethyl, n is selected from 0 and 1, $R_1$, $R_3$, $R_4$, $R_5$ and $R_6$ not simultaneously being H when $R_2$=phenyl, and the salts of the pyridyl containing compounds with pharmaceutically acceptable acids.

2. Pharmaceutical composition for the control of feeding behaviour comprising a pharmaceutically effective amount of a compound according to claim 1 in admixture with a pharmaceutically acceptable excipient.

3. Process for the preparation of a compound of formula I according to claim 1 and in which n=1, by oxidation of a compound of formula:

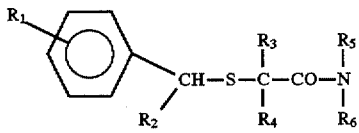

in which $R_1$, $R_2$, $R_3$, $R_4$, $R_5$ and $R_6$ have the meaning given in claim 1.

4. Process for the preparation of a compound according to claim 1, formula:

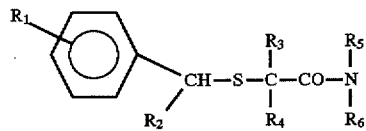

in which $R_1$, $R_2$, $R_3$, $R_4$, $R_5$ and $R_6$ have the meaning given in claim 1, by reaction of a reactive derivative of an acid of formula:

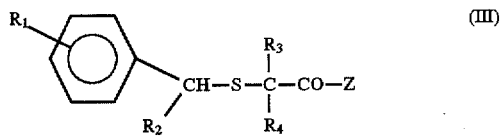

(III)

in which Z is a reactive group, with an amine of formula:

$HNR_5R_6$ (IV).

5. A compound of the formula:

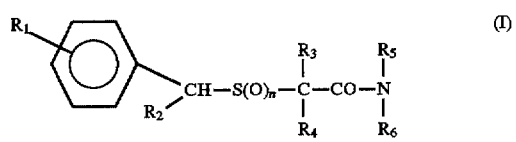

(I)

in which:

$R_1$ is H, $R_2$ is selected from phenyl and pyridyl, $R_3$ and $R_4$ are selected, independently of each other from H and methyl, $R_5$ and $R_6$ are selected, independently of each other, from H and pyridylmethyl or both represent an ethyl group, n is selected from 0 and 1, $R_1$, $R_3$, $R_4$, $R_5$ and $R_6$ not simultaneously being H when $R_2$ is phenyl, and the salts of the pyridyl containing compounds with pharmaceutically acceptable acids.

6. m-Chlorobenzhydrylsulfinylacetamide.

7. A method for controlling feeding behavior in a human, comprising administering an effective amount of a compound as claimed in claim 1.

8. A method for controlling feeding behavior in a human, comprising administering an effective amount of a compound as claimed in claim 5.

9. A method for controlling feeding behavior in a human, comprising administering an effective amount of a compound as claimed in claim 6.

* * * * *